United States Patent
Koehnke

Patent Number: 6,050,432
Date of Patent: *Apr. 18, 2000

[54] SEALABLE SLIP-IN BABY BOTTLE LINER

[76] Inventor: Diane Lynn Koehnke, 4639 Sun Valley Rd., Del Mar, Calif. 92014

[*] Notice: This patent issued on a continued prosecution application filed under 37 CFR 1.53(d), and is subject to the twenty year patent term provisions of 35 U.S.C. 154(a)(2).

[21] Appl. No.: 09/094,185

[22] Filed: Jun. 9, 1998

[51] Int. Cl.[7] .............................. A61J 9/00; B65D 23/02; B65D 33/24
[52] U.S. Cl. ..................... 215/11.3; 215/11.6; 383/63
[58] Field of Search .................. 215/11.1, 11.3, 215/11.5, 11.6; 383/63

[56] References Cited

U.S. PATENT DOCUMENTS

| | | | |
|---|---|---|---|
| 2,460,329 | 2/1949 | Allen et al. | 215/11.1 |
| 3,204,855 | 9/1965 | Boynton et al. | 215/11.3 |
| 4,501,585 | 2/1985 | Friedman | 215/11.3 X |
| 4,869,912 | 9/1989 | Mc Coy et al. | 215/11.3 X |
| 4,950,236 | 8/1990 | Wilson | 215/11.5 X |
| 5,356,398 | 10/1994 | Willis | 383/63 X |
| 5,385,251 | 1/1995 | Dunn | 215/11.3 |
| 5,509,549 | 4/1996 | Marandola | 215/11.3 |

*Primary Examiner*—Sue A. Weaver
*Attorney, Agent, or Firm*—Don E. Erickson

[57] ABSTRACT

A disposable, liquid-impermeable sterile plastic storage container for liquid infant foods, the container including an upper portion for receiving the liquid infant foods, the upper portion tapering into a lower portion for containing the liquid infant foods, the upper portion having an enlarged peripheral width relative to the lower portion with the lower portion of peripheral width less than an internal circumference of a baby feeding bottle. The container has complementarily opposed seal strips, which when engaged, prevent air ingress to the storage container. The upper and lower portions of the storage container are generally tubular cross-section, and the plastic of the storage container is selected to withstand temperatures lower than 32° F. In a preferred embodiment, the storage container the sealing means is re-sealable, and the sealing means is a Ziploc®. The storage container may have, in its lower portion, markings for fluid capacity.

16 Claims, 1 Drawing Sheet

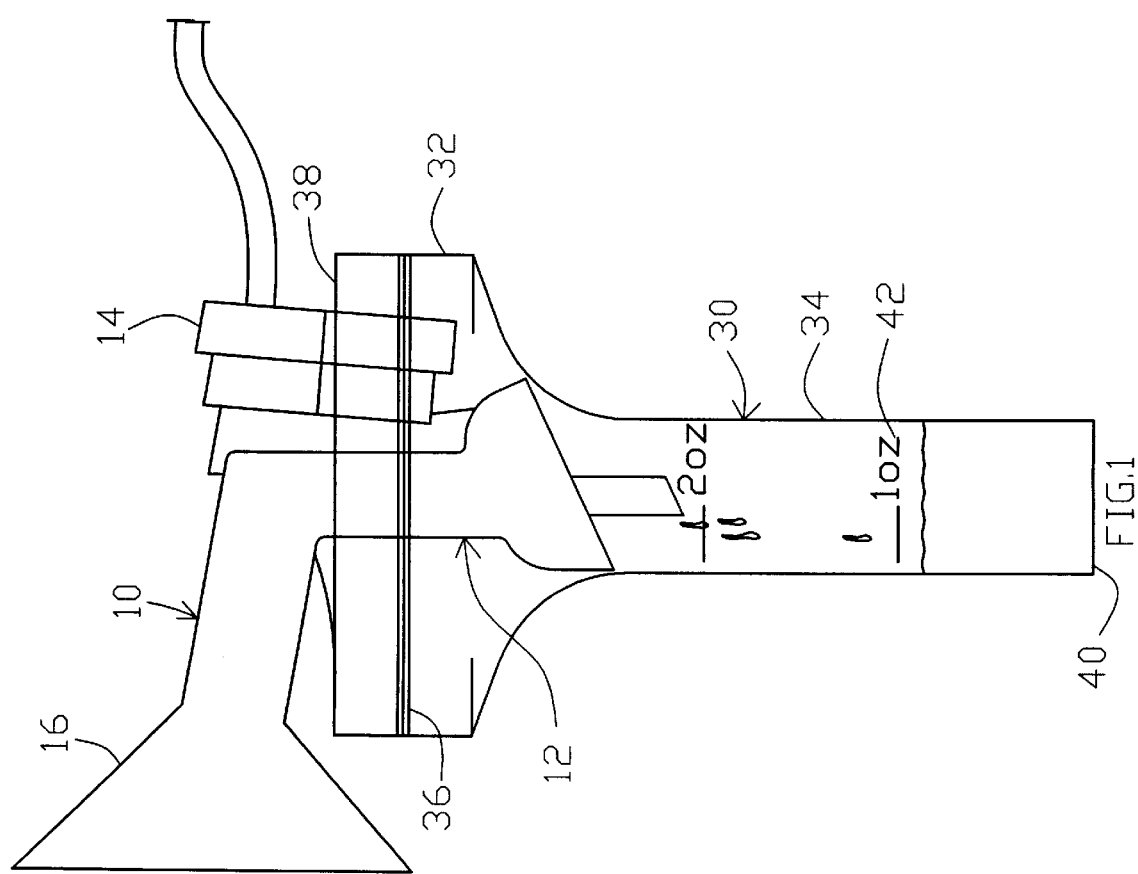

SEALABLE SLIP-IN BABY BOTTLE LINER

This application is related to Design patent application Ser. No. 29/082,000 filed by the inventor on Jan. 13, 1998.

The present invention generally pertains to a product that is useful for storing liquid baby foods, and more particularly to a storage container that may be placed in refrigeration. The invention more specifically pertains to a sterile, sealable, fluid-impervious plastic container for liquid baby foods that may be refrigerated and/or frozen.

BACKGROUND OF THE INVENTION

Scientific research has increasingly proved that it is more advantageous in the healthy development of an infant for the infant to be fed human breast milk. Human breast milk contains at least 100 ingredients that are not found in cow's milk and cannot be replicated in the laboratory. In addition, the composition of milk constantly changes to keep up with the baby's needs. Babies digest the protein and fat found in human breast milk easier than the protein and fat in cow's milk. The higher sodium and protein levels found in cow's milk put extra stress on a newborn's developing kidneys. Human breast milk contains low levels of phosphorous, a mineral that tends to slow the absorption of calcium. Babies are rarely allergic to their mothers' milk, but one out of 10 infants is allergic to cow's milk formula. Breast milk has a laxative effect on the baby and as a result, few breast-fed babies get constipated. Breast milk also seems to help the baby's digestive system fight off the microorganisms that cause diarrhea. Nursing mothers pass along antibodies to their babies and those antibodies help build up immunity to disease. As a result, breast-fed babies tend to come down with fewer colds, ear infections and other diseases.

The combination of an increased awareness of the health benefits of breast-feeding an infant and the increased number of women returning to the work force shortly after giving birth has led to an increased use of breast pumps for maintaining a supply of breast milk for the infant when the mother is unavailable. Banks of donors' breast milk have also been established to nourish needy infants. The breast milk must be stored in a container which is fluid impermeable. This means that the breast milk should not be able to leak from the container, nor should air be able to penetrate the container. Air access to the breast milk will result in the milk being spoiled. In addition, the container must be able to withstand temperatures below 32° Fahrenheit.

Heretofore there have been numerous types of containers and baby bottle liners developed for storage of liquid baby foods. However, up to now, no one has developed a storage container for mother's milk, and other liquids which must be kept sterile, which may be easily filled, and which may be placed directly in the refrigerator or freezer without additional storage apparatus. Typically, milk is withdrawn from a mother's breast by means of a breast pump into an intermediary container. The mother's milk is then decanted into a freezer proof rigid container, capped, and then placed in a special storage rack in the refrigerator or freezer.

Disposable bags of a nylon/polyethylene laminate have been developed to reduce the loss of nutrients when the milk is stored over a long period of time. When the mother wishes to utilize a nurser to feed her own breast milk to her child, it has been necessary for the mother to express the milk by hand, or by means a breast pump, into the disposable liner and then transfer the extracted milk by hand from the liner to the nurser. This procedure is time-consuming, messy and unsanitary, since unwanted elements may be introduced in the transfer of the milk from the pump container to the nurser.

Infant nursers, such as those manufactured and sold under the PLAYTEX trademark, consisting of a disposable polyethylene plastic liner fitted inside a rigid, reusable plastic shell, have become very popular due the convenience and added cleanliness and safety which comes from not having to wash and reuse the baby's bottle, however the PLAYTEX liner is not sealable, nor can it be stored in a refrigerator. Recently, Munchkin, Inc, has manufactured and sold a drop-in disposable bottle which may be stored in the refrigerator. This storage bottle, in order to prevent leakage of the stored milk from the bottle, must be maintained in an upright position in the refrigerator or freezer, and the storage bottle is sold with a rack for holding such storage bottle in the upright position. Since the storage bottle must be maintained in the upright position to avoid leakage from the bottle, the sealing means for the bottle is not fluid-impermeable.

Another recent product is the Mothers Milk Storage Bags®, which consists of a tubular plastic bag which includes, at its receiving end, a clamping means for closing the bag consisting of a semi-rigid, flexible strip at the periphery of the receiving end. The instructions for closing the bag include folding the bag about the clamping means for at least four turns, then employing the clamping means. Empirical tests reveal that such means of clamping still do not prevent liquid from leaking from the bag, thus the bag is not fluid impermeable.

SUMMARY OF THE INVENTION

The present invention provides a disposable, sterile, fluid-impermeable plastic storage container for liquid infant foods. The container consists of an upper portion for receiving the liquid infant foods, the upper portion tapering into a lower portion for containing the liquid infant foods. The upper portion has an enlarged peripheral width relative to the lower portion. The enlarged upper portion enables the container to be placed over a standard fluid dispensing port of a breast pump, and then, when the fluid is to be consumed, folded over the lip of a baby feeding bottle. The lower portion of the container has a peripheral width less than an internal circumference of the baby feeding bottle to enable for ease of insertion in the bottle. The upper and lower portions of the container may be constructed of generally tubular cross-section. The storage container is preferably made of a plastic selected to withstand temperatures lower than 32° F.

The peripheral width of the upper portion has a hermetic re-sealable means for preventing fluid permeation to and from the storage container. The storage container may have markings for fluid capacity.

The present invention obviates the disadvantages associated with the previous bottles and liners by providing an improved disposable container that is convenient to use and which can be easily and economically manufactured. The container is preferably constructed of flexible, non-breakable material, e.g., plastic, and includes, integral to the container, a fluid-impermeable seal, permitting the container to be stored without the use of special racks. Although it has been long recognized that breast milk must be sealingly stored, none of the prior art has contemplated the use of a Ziploc® in combination with the container of the invention.

The present invention has many advantages over the prior art. The container of the invention may be adapted to be secured over the outlet of a standard breast pump during use, thereby eliminating the need to transfer the breast milk from an intermediary container into a refrigerable container, and thereby significantly reducing the opportunity for contamination of the milk. In addition, since the container of the invention is hermetically sealable, there are no special racks, or supports, required for the container when placed in refrigeration. Further, the container of the invention may be directly placed in the freezer section of a refrigerator, without fear of leakage or contamination.

All the advantages specifically stated herein do not necessarily apply to every conceivable embodiment of the invention. Further, such stated advantages of the invention are only exemplifications and should not be construed as the only advantages of this consequential invention. Additional features of the present invention are described with reference to the drawings and detailed description of the preferred embodiments.

BRIEF DESCRIPTION OF THE DRAWINGS

FIG. 1 is an elevation view of the collection and dispensing portion of a breast pump with the container of the invention disposed about the fluid dispensing port of the pump.

FIG. 2 is an elevation view of the container of the invention disposed in and about a common baby feeding bottle.

DETAILED DESCRIPTION

FIG. 1 shows the collection and dispensing portion of a typical breast pump 10 (not part of the invention) with the container 30 disposed about the fluid dispensing port 12 of the pump. The pump contains a means of providing suction to the breast 14, and a suction cup 16 for mating against the breast (not shown) and for sealingly encapsulating the mother's nipple. Although a breast pump is described, breast milk alternately may be manually squeezed from the breast directly into container 30. The container 30 is comprised of an upper portion 32 and a lower portion 34. In the preferred embodiment, both upper portion 32 and lower portion 34 are of generally tubular design. The upper portion 32 is sized to receive the fluid dispensing port 12 of breast pump 10. A peripheral width of about 3.5 inches is sufficient for this purpose. The upper portion 32 includes sealing means 36 extending across the peripheral width of upper portion 32, in generally parallel displacement from upper surface 38 of the container. Upper portion 32 tapers into a lower portion 34, sized to fit within a standard baby feeding bottle, has a periperal width of about 1.125 inches. Lower portion 30 is sealed at its lowest extremity 40. In the exemplary embodiment, the overall length of container 30 is about 5.5 inches from upper surface 38 to lowest extremity 40. Such overall length permits the upper portion 32 of container 30 to be folded over the lip 52 of a typical baby feeding bottle 50, as shown in FIG. 2. When container 30 is inserted in feeding bottle 50, and upper portion 32 folded over the lip 52. standard cap and nipple 54 may be screwed onto feeding bottle 50.

"One of ordinary skill in the packaging arts would know that a Ziploc® consists of a pair of complementarily opposed seal strips, one strip comprising a vane component, and the second strip comprising a channel component, and when such strips are engaged, form a liquid impermeable barrier, generally as described in U.S. Pat. No. Re.28,969."

Sealing means 36 is a hermetic barrier, impermeable to fluids, thereby precluding air from penetrating into container 30, and preventing breast milk from leaking from container 30. In a preferred embodiment sealing means 36 is a Ziploc®, although it is contemplated that equivalent sealing means existing, or developed in the future, could be used. The only criteria for such sealing means is that it must be fluid impermeable.

An advantage of a Ziploc®, or equivalent means, is that the Ziploc® is re-usable. The Ziploc® may be used to tighten container 30 about fluid dispensing port 12 of breast pump 10, thereby facilitating and simplifying the use of container 30. Once container 30 is filled to the desired level, the Ziploc® can then be sealingly closed and container 30 placed in the refrigerator or freezer for storage.

Container 30 is constructed from a plastic selected to withstand temperatures lower than 32° F. Such plastics are typically polypropylene or polyethylene, of which there are several manufacturers. The manufacturing process for container 30 is a process well known in the art. and the interior surfaces of container 30 are sterilized during such process. In addition, lower portion 34 of container 30 may be marked 42 to indicate the fluid capacity of the contents.

While the present description contains many specificities, these should not be construed as limitations on the scope of the invention., but rather as an exemplification of one preferred embodiment thereof. Many other variations are possible, for example, overall dimensions of container 30 may be varied for receiving differing amounts of fluids. Container 30 of the exemplary embodiment was sized to contain approximately 2 ounces of fluid in its lower portion 34, which amount is typically consumed by an infant in one feeding. However, container 30 could be sized for larger/smaller amounts of fluids. Concomitantly, the geometric structures of upper portion 32 and or lower portion 34 are not limited to tubular, but could be of any useful geometry. Accordingly, the scope of the invention should not be determined by the specific embodiment/s illustrated herein, but the full scope of the invention is further illustrated by the claims appended hereto.

I claim:

1. A disposable, liquid-impermeable plastic storage container for liquid infant foods, the container comprising:
   (a) an upper portion for receiving the liquid infant foods, the upper portion tapering into a lower portion for containing the liquid infant foods, the upper portion having an enlarged peripheral width relative to the lower portion;
   (b) the lower portion of peripheral width less than an internal circumference of a baby feeding bottle; and
   (c) the peripheral width of the upper portion having incorporated therewithin a reusable hermetic sealing means for preventing fluid permeation to and from the storage container.

2. The storage container of claim 1 wherein the upper portion is of generally tubular cross-section.

3. The storage container of claim 1 wherein the lower portion is of generally tubular cross-section.

4. The storage container of claim 1 wherein the plastic is selected to withstand temperatures lower than 32° F.

5. The storage container of claim 1 wherein the lower portion has markings for fluid capacity.

6. The storage container of claim 1 wherein the container is sterile.

7. The storage container of claim 1 wherein the upper portion is sized to encapsulate a fluid dispensing port of a breast pump.

8. The storage container of claim 1 wherein the sealing means is re-sealable.

9. The storage container of claim 8 wherein the sealing means are first and second complementarily opposed seal strips, the first strip comprising a vane component, and the second strip comprising a channel component, and wherein when such strips are engaged, they form an impermeable barrier.

10. A disposable, liquid-impermeable plastic storage container for liquid infant foods, the container comprising:
  (a) an upper portion for receiving the liquid infant foods, the upper portion of generally tubular cross-section, the upper portion tapering into a lower portion for containing the liquid infant foods, the upper portion having an enlarged peripheral width relative to a peripheral width of the lower portion, the upper portion is sized to encapsulate a fluid dispensing port of a breast pump;
  (b) the lower portion of generally tubular cross-section, the lower portion having a peripheral width less than the internal circumference of a baby feeding bottle;
  (c) the peripheral width of the upper portion having incorporated therewithin a hermetic re-sealable sealing means for preventing fluid permeation to and from the storage container, and wherein the plastic is selected to withstand temperatures lower than 32° F.

11. The storage container of claim 10 wherein the lower portion has markings for fluid capacity.

12. The storage container of claim 10 wherein the container is sterile.

13. The storage container of claim 10 wherein the sealing means are first and second complementarily opposed seal strips, the first strip comprising a vane component, and the second strip comprising a channel component, and wherein when such strips are engaged, they form an impermeable barrier.

14. A disposable, liquid-impermeable plastic storage container for liquid infant foods, the container comprising:
  (a) an upper portion for receiving the liquid infant foods, the upper portion of generally tubular cross-section, the upper portion tapering into a lower portion for containing the liquid infant foods, the upper portion having an enlarged peripheral width relative to a peripheral width of the lower portion, the upper portion sized to encapsulate a fluid dispensing port of a breast pump;
  (b) the lower portion of generally tubular cross-section, the lower portion having a peripheral width less than an internal circumference of a baby ceding bottle, the lower portion having markings for fluid capacity; and
  (c) the peripheral width of the upper portion having incorporated therewithin a hermetic sealing means for preventing fluid permeation to and from the storage container; and wherein the plastic is selected to be sterile and to withstand temperatures lower than 32° F.

15. The storage container of claim 14 wherein the sealing means is re-sealable.

16. The storage container of claim 15 wherein the sealing means are first and second complementarily opposed seal strips, the first strip comprising a vane component, and the second strip comprising a channel component, and wherein when such strips are engaged, they form an impermeable barrier.

* * * * *